United States Patent
Vaughnn

(10) Patent No.: US 7,724,358 B2
(45) Date of Patent: May 25, 2010

(54) ILLUMINATOR FOR DARKFIELD INSPECTION

(75) Inventor: David Vaughnn, Edina, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 12/276,065

(22) Filed: Nov. 21, 2008

(65) Prior Publication Data

US 2009/0073429 A1    Mar. 19, 2009

Related U.S. Application Data

(63) Continuation of application No. 11/179,010, filed on Jul. 11, 2005, now abandoned.

(60) Provisional application No. 60/587,206, filed on Jul. 12, 2004.

(51) Int. Cl.
*G01N 21/00*    (2006.01)

(52) U.S. Cl. .................. 356/237.2; 359/201.1

(58) Field of Classification Search ........................ None
See application file for complete search history.

(56) References Cited

U.S. PATENT DOCUMENTS

| | | | |
|---|---|---|---|
| 1,539,579 A | 5/1925 | Kucharski | |
| 4,893,932 A * | 1/1990 | Knollenberg | ............. 356/237.3 |
| 5,153,668 A | 10/1992 | Katzir et al. | |
| 5,539,514 A * | 7/1996 | Shishido et al. | ............ 356/237.4 |
| 6,630,996 B2 | 10/2003 | Rao et al. | |
| 7,327,450 B2 * | 2/2008 | Kreh et al. | ................ 356/237.5 |
| 2005/0052644 A1 * | 3/2005 | Lewis et al. | ............... 356/237.4 |

* cited by examiner

*Primary Examiner*—Gregory J Toatley, Jr.
*Assistant Examiner*—Juan D Valentin
(74) *Attorney, Agent, or Firm*—Dicke, Billig & Czaja, PLLC

(57) ABSTRACT

Light from a single source is divided among several illumination arms, each of which directs light via a multimode fiber bundle from the source to the wafer location. The arms are arranged circumferentially around a common illumination region, so that the region is illuminated from several directions. For each arm, light exiting the fiber bundle enters a turning prism, reflects off the hypotenuse of the prism, and is diverged in one dimension by a negative cylindrical surface on the exiting face of the prism. The beam then reflects off an anamorphic mirror and propagates to the illumination region on the wafer. The beam has an asymmetric footprint, so that it illuminates a nearly circular region of the wafer when viewed at normal incidence. The fiber bundle is at the front focal plane in the meridional dimension. The illumination region is at the rear focal plane in both dimensions.

13 Claims, 8 Drawing Sheets

| | Fiber | Negative Cylinder | Reflector | Target | Total power |
|---|---|---|---|---|---|
| Radius in x, Rx [mm] / Radius in y, Ry [mm] | | 1.375371 #DIV/0! | -17.7724 -131.666 | | |
| Thickness before surface, t [mm] / Thickness after surface, t' [mm] / Refractive index before surface, n / Refractive index after surface, n' | 0.474 | 0.474 8.665827 | 8.665827 -65.8328 | -65.8328 | |
| Power in x, phix [mm-1] / Power in y, phiy [mm-1] | 1.855847 | 1 1.855847 | -0.62227 0 | 0.112534 0.01519 | -1 -1 |
| | | | | | 0.097101 / 0.01519 |
| Numerical aperture of fiber bundle, NA / Half-angle of x-cone incident on target [deg] / Half-height of fiber bundle, H [mm] / Half-height of illumination at target, F [mm] / Tilt of target from normal incidence, I [deg] / Cosine of target tilt angle, cos I | | | | | 0.01519 / 2.5 / 0.449643 / 10 / 81 / 0.156434 |

Center of fiber bundle, center of target

| Ray height in x, y [mm] / Ray angle before surface in x, u [radians] / Ray angle after surface in x, u' [radians] | 0 0 0 | 0 0 0 | 0 0 0 | 0 0 | |
| Ray height in y, y [mm] / Ray angle before surface in y, u [radians] / Ray angle after surface in y, u' [radians] | 0 0 0 | 0 0 0 | 0 0 0 | 0 0 | |

Center of fiber bundle, +edge of target

| Ray height in x, y [mm] / Ray angle before surface in x, u [radians] / Ray angle after surface in x, u' [radians] | 0 0.1519 0.081849 | 0.038797 0.081849 0.176042 | 1.564345 0.176042 2.78E-17 | 1.564345 2.78E-17 | Ray 3 |
| Ray height in y, y [mm] / Ray angle before surface in y, u [radians] / Ray angle after surface in y, u' [radians] | 0.1519 0.081849 | 0.038797 0.081849 0.1519 | 1.355136 0.1519 -0.13132 | 10 -0.13132 | Ray 1 |

+Edge of fiber bundle, -edge of target

| Ray height in x, y [mm] / Ray angle before surface in x, u [radians] / Ray angle after surface in x, u' [radians] | 0.449643 -0.1519 -0.08185 | 0.410846 -0.08185 0.103756 | 1.309977 0.103756 0.043661 | -1.56434 0.043661 | |
| Ray height in y, y [mm] / Ray angle before surface in y, u [radians] / Ray angle after surface in y, u' [radians] | 0.449643 -0.1519 -0.08185 | 0.410846 -0.08185 -0.1519 | -0.90049 -0.1519 0.138146 | -10 0.138146 | |

+Edge of fiber bundle, center of target

| Ray height in x, y [mm] / Ray angle before surface in x, u [radians] / Ray angle after surface in x, u' [radians] | 0.449643 0 0 | 0.449643 0 0 | 2.874321 0.279798 0.279798 | -5.3E-15 0.043661 0.043661 | Ray 4 |
| Ray height in y, y [mm] / Ray angle before surface in y, u [radians] / Ray angle after surface in y, u' [radians] | 0.449643 0 0 | 0.449643 0 0 | 0.449643 0 0.00683 | 0 0.00683 | Ray 2 |

+Edge of fiber bundle, +edge of target

| Ray height in x, y [mm] / Ray angle before surface in x, u [radians] / Ray angle after surface in x, u' [radians] | 0.449643 -0.1519 0.081849 | 0.48844 0.081849 0.45584 | 4.438666 0.45584 0.043661 | 1.564345 0.043661 | |
| Ray height in y, y [mm] / Ray angle before surface in y, u [radians] / Ray angle after surface in y, u' [radians] | 0.449643 0.1519 0.081849 | 0.48844 0.081849 0.1519 | 1.804779 0.1519 -0.12449 | 10 -0.12449 | |

Fig. 10

ILLUMINATOR FOR DARKFIELD INSPECTION

CROSS-REFERENCE TO RELATED APPLICATIONS

This application is a continuation of U.S. patent application Ser. No. 11/179,010, filed Jul. 11, 2005, which claims priority under 35 U.S.C. §119(e)(1) to U.S. Provisional Patent Application Ser. No. 60/587,206, filed Jul. 12, 2004; the entire teachings of which are incorporated herein by reference.

FIELD

The present disclosure relates to inspection of materials, and more particular to illuminators for dark-field inspection of material, inspection systems for dark-field inspection of material, and methods for illuminating a target for dark-field inspection.

DESCRIPTION OF RELATED ART

As more manufacturing processes use wafer-based technology, and utilize increasingly smaller features on these wafers, it becomes increasingly important to inspect the wafers for defects at various stages throughout the manufacturing process. Wafer inspection systems have evolved to keep pace with these demanding requirements.

In a typical wafer inspection system, a wafer is attached to a movable stage that translates the wafer underneath an inspection camera. The camera acquires an image of a portion of the wafer and processes it using known image processing techniques. Any defects in the field of view are either marked on the wafer by the inspection system, or noted in a data file, so that the defect may be corrected or avoided during subsequent manufacturing steps. The translation stage then moves the wafer to the next location, and the process is repeated until the entire usable area of the wafer is inspected. This inspection process improves yields and efficiency by identifying or removing defective material as early as possible in the manufacturing process.

One class of inspection system especially suited for the inspection of bare, flat, or featureless wafers is known as "dark-field". In a dark-field inspection system, the illumination takes place at angles of incidence that are not specularly reflected into the imaging optics. If there are no three-dimensional features or defects in the field of view on the wafer, the illumination beam undergoes a specular reflection, and is not captured by the imaging optics. In other words, in a dark-field system, a defect-free wafer appears dark to the imaging camera. A small particle, say 5 microns in size, reflects or scatters some light in various directions, including a fraction that enters the imaging camera. Therefore, a small particle or defect shows up as a bright spot in the field of view of a dark-field system. A dark field system may also be used for wafers with features on them.

The illumination for a dark-field system greatly affects the overall performance of the inspection system. For instance, a "ring-lamp" device, similar to those used to illuminate dark-field microscopes, does not work very well for the dark-field wafer inspection systems. They typically have neither uniform illumination over the field nor a uniform angular spectrum over the field. As a result, the sensitivity of the inspection system can vary over the field of view, which is highly undesirable. This variation in sensitivity can require additional processing time for each image, thereby slowing down the system and reducing efficiency.

SUMMARY

Advantageously, the present disclosure provides for a dark-field illumination system that is compact, or illuminates a large illumination region on the target, or provides uniform illumination and a uniform angular spectrum across an illumination region on the target, or has a low range of incident angles and a broad circumferential azimuth for an illumination region on the target, or is bright throughout an illumination region on the target. The various embodiments respectively achieve one or more of these advantages.

One embodiment of the present disclosure is an illuminator for dark field inspection of a surface of a target, the illuminator comprising a plurality of illumination arms disposed about an illumination region, and each of the arms comprising: an extended, substantially uniform source of diverging light; a turning element having a first face optically coupled to the light source, and a second face having cylindrical optical power in a meridional direction; and an anamorphic element having a first optical power in an azimuthal direction and a second optical power in the meridional direction, the first and second optical powers being unequal, and the anamorphic element being optically coupled to the second face of the turning element.

Another embodiment of the present disclosure is an illuminator for dark field inspection of a surface of a target, the illuminator comprising a plurality of illumination arms disposed about a substantially circular illumination region substantially at the target surface, and each of the arms comprising: an extended, substantially uniform source of diverging light; a coupling element having an incident face optically coupled to the light source, and an exiting face with negative cylindrical optical power in an meridional direction; and an anamorphic element having a first optical power in an azimuthal direction and a second optical power in the meridional direction, the first and second optical powers being unequal, and the anamorphic element being optically coupled to the exiting face of the coupling element; wherein each of the arms has an azimuthal front focal plane, an azimuthal rear focal plane, a meridional front focal plane, and a meridional rear focal plane; and wherein for each of the arms: the azimuthal front focal plane and the meridional front focal plane are not coincident; the light source is located substantially at the meridional front focal plane; the meridional rear focal plane and the azimuthal rear focal plane are substantially coincident; the illumination region has a center located substantially at the meridional rear focal plane and at the azimuthal rear focal plane; and the light source, turning element, and anamorphic element are arranged to illuminate the illumination region at a non-zero angle, or range of angles, of incidence relative to a normal of the illumination region to achieve specular reflection from the target surface under defect-free conditions.

Another embodiment of the present disclosure is an illuminator for dark field inspection of a surface of a target, the illuminator comprising a plurality of illumination arms disposed about an illumination region substantially at the target surface, and each of the arms comprising: an extended, substantially uniform source of diverging light; and an assembly of optical elements for producing from the diverging light an illuminating beam directed to the illumination region, the illuminating beam having a nominal incident angle, an incident angle range, and an azimuthal angle range; wherein both the nominal incident angle and incident angle range are essentially invariant throughout the illumination region; wherein the azimuthal angle range is essentially invariant throughout the illumination region; and wherein light intensity throughout the illumination region is essentially invariant.

Another embodiment of the present disclosure is an illuminator for dark field inspection of a surface of a target, the illuminator comprising a plurality of illumination arms disposed about a substantially circular illumination region substantially at the target surface, and each of the arms comprising: means for establishing an azimuthal rear focal plane; means for establishing a meridional rear focal plane, the meridional rear focal plane and the azimuthal rear focal plane being substantially coincident; means for establishing an azimuthal front focal plane; means for establishing a meridional front focal plane separated from the azimuthal front focal plane; means for locating a center of the illumination region substantially at the meridional rear focal plane and at the azimuthal rear focal plane; means for introducing light having extended, substantially uniform, and diverging characteristics substantially at the meridional front focal plane; and means for forming a beam from the light introduced at the meridional front focal plane, the beam being incident on the illumination region at a non-zero angle of incidence relative to a normal of the illumination region to achieve specular reflection from the target surface under defect-free conditions.

Another embodiment of the present disclosure is a method for illuminating an illumination region on a surface of a target from a plurality of different directions with respective optical systems to perform a dark field inspection of the target surface, comprising for each of the optical systems: establishing an azimuthal rear focal plane; establishing a meridional rear focal plane, the meridional rear focal plane and the azimuthal rear focal plane being substantially coincident; establishing an azimuthal front focal plane; establishing a meridional front focal plane separated from the azimuthal front focal plane; establishing the illumination region as a substantially circular region with a center substantially at the meridional rear focal plane and at the azimuthal rear focal plane; introducing light having extended, substantially uniform, and diverging characteristics substantially at the meridional front focal plane; and forming a beam from the light introduced at the meridional front focal plane, the beam being incident on the illumination region at a non-zero angle of incidence relative to a normal of the illumination region to achieve specular reflection from the target surface under defect-free conditions.

Another embodiment of the present disclosure is A wafer inspection system comprising: a fiber optic dark-field illuminator comprising: a source of spectrally filtered, spatially uniform, extended and diverging light; and a plurality of illumination arms optically coupled to the light source and circumferentially disposed about a substantially circular illumination region; and a camera disposed at normal or near-normal incidence with respect to the illumination region, the illumination region being within a field of view of the camera, and the camera comprising a collection lens having a numerical aperture that defines a maximum collection angle of light for the collection lens; wherein each of the illumination arms comprises: a turning element having an incident face optically coupled to the light source, and an exiting face with negative cylindrical optical power in a meridional direction; and an anamorphic mirror having a first optical power in an azimuthal direction and a second optical power in the meridional direction, the first and second optical powers being unequal, and the anamorphic mirror being optically coupled to the exiting face of the turning prism; wherein each of the illumination arms has an azimuthal front focal plane, an azimuthal rear focal plane, a meridional front focal plane, and a meridional rear focal plane; and wherein for each of the arms: the azimuthal front focal plane and the meridional front focal plane are not coincident; the light source coupling is located substantially at the meridional front focal plane; the meridional rear focal plane and the azimuthal rear focal plane are substantially coincident; the illumination region has a center located substantially at the meridional rear focal plane and at the azimuthal rear focal plane; and the light source coupling, turning element, and anamorphic mirror are arranged to illuminate the illumination region at an angle of incidence relative to a normal of the illumination region that is greater than the maximum collection angle.

BRIEF DESCRIPTION OF THE DRAWINGS

FIG. 10 is a spreadsheet showing a numerical paraxial raytrace of the system of FIG. 8.

DETAILED DESCRIPTION

Figure 1:
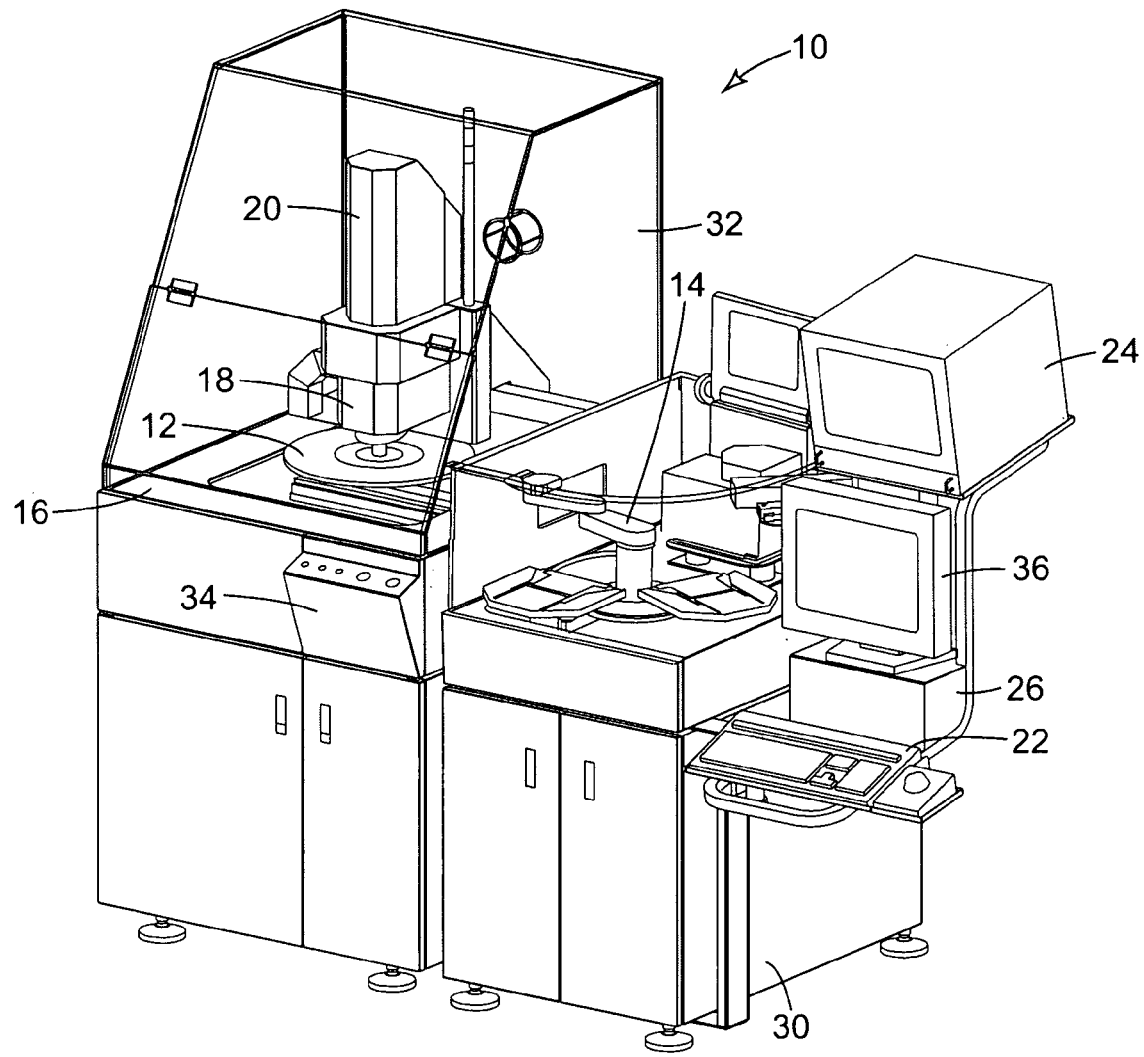
FIG. 1 is a perspective drawing of a wafer inspection system.

The present disclosure is directed to illuminators for darkfield inspection systems, which are commonly used in systems that visually inspect wafers for defects during a particular manufacturing process. An example of a wafer inspection system is shown in FIG. 1.

A typical wafer inspection system 10 is used in one environment to inspect whole wafers before die have been fabricated on them, but may also be used to inspect patterned whole wafers, die diced from patterned wafers, sawn wafers, broken wafers, wafers of any kind on film frames, die in gel paks, die in waffle paks, MCMs, JEDEC trays, Auer boats, and other wafer and die configurations, whether or not packaged. Hereafter, all of these uses shall be referred to generally as inspection of wafers. System 10 includes a wafer test plate 12, an actuator 14 that moves the wafer to the test plate 12, a wafer alignment device 16 for aligning each and every wafer at the same x, y, and angular location or x, y, z, and angular location, a focusing mechanism 18, a camera 20 or other visual inspection device for visual inputting of good wafers during training and for visual inspection of other unknown quality wafers during inspection, a user console 22 for inputting parameters and other constraints or information such as sensitivity parameters, geometries, die size, die shape, die pitch, number of rows, number of columns, etc., a display 24 for displaying the view being seen by the camera presently or at any previously saved period, a computer system 26 or other computer-like device having processing and memory capabilities for saving the inputted good die, developing a model therefrom, and comparing or analyzing other die in comparison to the model, a frame 30, a hood 32, a control panel 34, a system parameters display 36, objective 38, and a fiber optic dark field illuminator 40.

Figure 2:
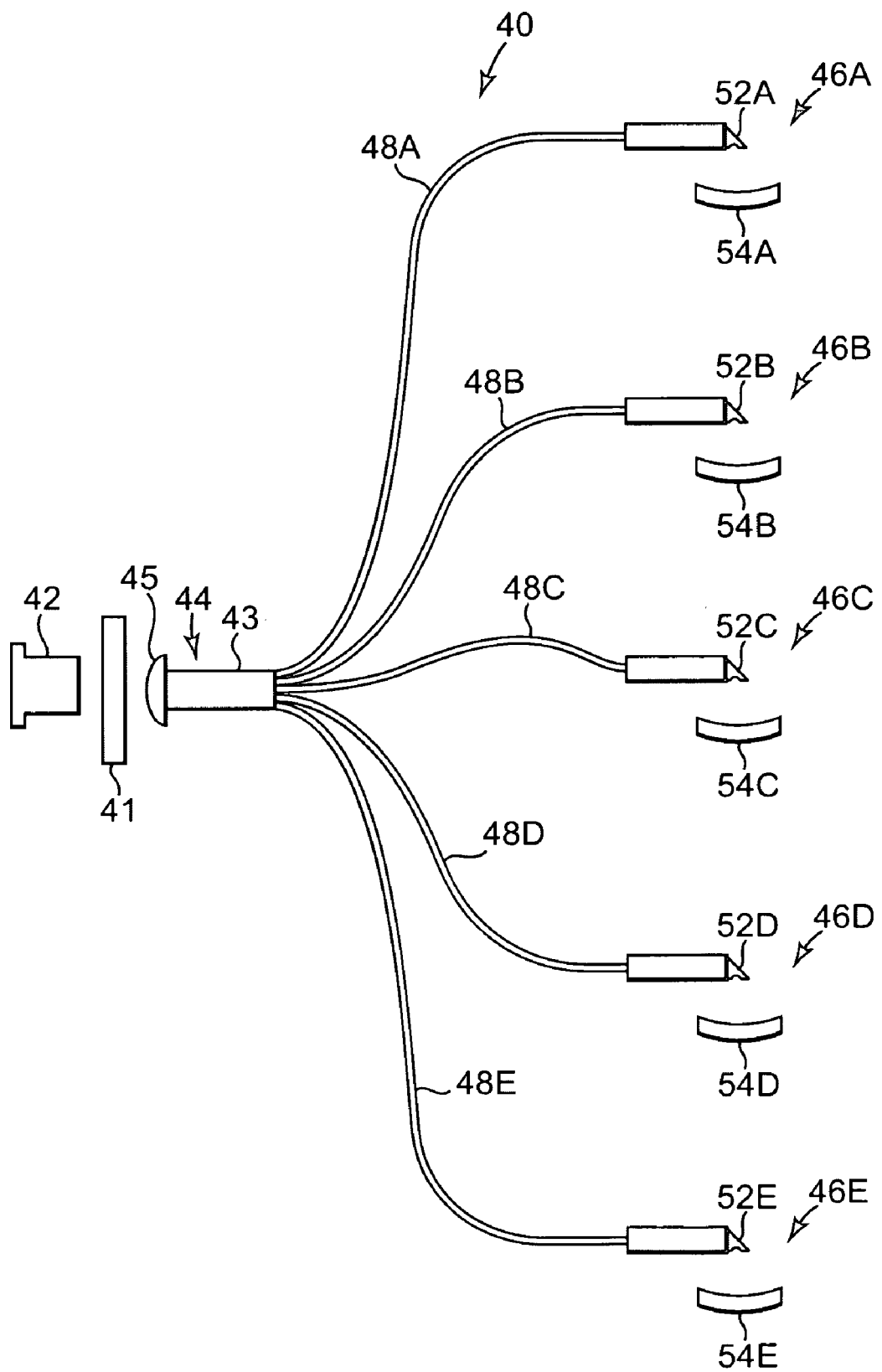
FIG. 2 is a plan drawing of an illumination system.

Generally, a dark field illuminator may have one or more illumination arms, each having a light source. In one embodiment, the dark field illuminator has a single light generating element, the output of which may be spectrally filtered, collected, made spatially uniform, and/or divided among one or more illumination arms. Alternatively, each illumination arm may be provided with its own light generating element, the output of which may be spectrally filtered, collected, and made spatially uniform. In those embodiments where multiple illumination arms are provided as illustrated in FIG. 2, each illumination arm emits light from a particular position around the circumference of an illumination region to illuminate the illumination region, with enough spatial clearance for a turret of lenses for an inspection camera and various other mechanical elements. Note that while five illumination arms are illustrated, it is to be understood that more or fewer arms may be provided. Generally, the illumination arms may be located in any desired manner with respect to the illumination region, provided that the illumination is delivered at a fairly high angle of incidence relative to the surface normal from each illumination arm to illuminate the illumination region so that a specular reflection from the wafer is not normally collected by the imaging optics. In this manner, a no-defect condition appears as darkness in the visual field, hence the name "dark field". The numerical condition for dark field illumination is as follows: if the collection (or imaging) optics have a characteristic numerical aperture NA, which defines the maximum angle at which light can enter the collection optics, then the dark field illumination system should supply light at an effective numerical aperture larger than NA, so that it does not enter the collection optics for a specular reflection.

Note that in general, a dark field system need not be constrained to the condition in which the collection optics are oriented at near-normal incidence and the illumination optics are at a higher angle of incidence, located "outside" the field of the collection optics. For instance, the locations of the illumination and collection systems may be reversed, with the illumination system surrounded by the collection system. Or, particular angles or orientation may be physically blocked in the pupil of the lens. For the purposes of this document, the collection optics are oriented at near-normal incidence, and the illumination optics are oriented at near-grazing incidence, well outside the numerical aperture of the collection optics.

For an optimal signal-to-noise ratio, it is desirable to maximize the gap between the maximum collection angle and the minimum illumination angle. For instance, if the collection optics have a numerical aperture of 0.8, then they collect all the light in the field of view having a propagation angle less than 53°. If the illumination system supplies light at an incident angle of 81°±2.5°, then the minimum illumination angle is 78.5°, and the angular separation between the illumination and the collection bands is 25.5°. This relatively large angle improves the signal-to-noise ratio for detecting small objects or particles in the field of view.

Note that for the purposes of this document, the illumination region is defined as the area to be illuminated when the system is operational. It will be understood that even when the system is not operational or the light source is between pulses, the illumination region still exists, even though it is not receiving light from the source.

A schematic drawing of the illuminator 40 is shown in a disassembled state in FIG. 2. Light is produced for the illumination system by a light source, which is one embodiment, a strobe lamp 42. The strobe lamp 42 is activated to illuminate the illumination region for a short period of time each time a picture is taken by the camera (FIG. 1, element 20). Use of such a strobe lamp 42 is effective at reducing the blur that might occur if a continuously operating light source were used with a wafer that was subject to movements from the translation stage. In one embodiment, the lamp contains a fairly broad spectrum of wavelengths, but may be adapted to output a more narrow spectrum of wavelengths where so desired.

Upon leaving the strobe lamp 42, the beam passes through a wavelength-sensitive filter 41, which blocks wavelengths in the range of about 280 nm to 400 nm, and passes wavelengths longer than about 400 nm. This wavelength range is merely exemplary, and any suitable filter may be used. Alternatively, the filter may be omitted.

The wavelength-filtered beam then enters a condenser lens 45, which may be spherical or aspheric, and may be coated with an antireflection thin film coating. The condenser lens 45 directs the beam into a mixing bar 43, which is effectively a long, skinny, transparent parallelepiped. Light enters one of the longitudinal ends of the mixing bar 43 and bounces through total internal reflection until it leaves the mixing bar 43 at the other longitudinal end. The output from the mixing bar 43 is essentially uniform in intensity, and also essentially uniform in angular spectrum within a particular numerical aperture.

The combination of the condenser lens 45 and the mixing bar 43 may be referred to as the head 44.

The output from the mixing bar 43 is coupled into multiple fiber bundles 48, where each fiber bundle 48 directs a beam with its own set of optics onto the illumination region. In some embodiments, the illumination region defines all or a portion of wafer of the type used in the manufacture of semiconductor and micro-electromechanical devices. The fibers used in the bundle are in some embodiments multi-mode fibers that efficiently couple in light within a particular numerical aperture. To get efficient coupling from the mixing bar 43 to the fiber bundles 48, the numerical aperture of the fiber bundles 48 may be matched to the numerical aperture of the beam exiting the mixing bar 43. The fibers are arranged in a bundle, which may be round or some other convenient shape, and may have different shapes or arrangements at each end.

The fiber bundles 48 direct the light toward a wafer or other object within the illumination region, and are arranged to encircle the camera and direct light toward the illumination region at a large angle of incidence. The illumination optics are designed to allow for a large clearance so that the camera and other mechanical elements have enough room to operate or be adjusted.

Each fiber bundle 48 is coupled to a right-angle prism 52, which turns a beam exiting the bundle 90° after a reflection off the prism hypotenuse. The exiting face of the prism has a negative cylindrical surface, which diverges the beam in the x-direction and leaves the beam largely unchanged in the y-direction. Such a prism is straightforward to manufacture, and is typically made first as a 45/45/90 prism, upon which the cylindrical surface is then ground and polished. Alternatively, a cylindrical lens may be attached to the exiting prism face, so that the cylindrical surface does not have to be manufactured directly on the prism. The 90° angle as shown is preferred, so that the entire optical path can fit inside a fairly small volume in the machine. Although a 90° turning prism is shown, any other suitable turning angle may be used. Likewise, any other suitable prism may be used, with any number of internal bounces, including no bounces. Alternatively, the turning prism may be replaced by an element that does not turn the beam at all, but merely has a cylindrical optical power. For instance, a cylindrical lens may be attached to the fiber bundle without a prism at all.

The beam then reflects off an anamorphic mirror 54, which has different powers in the x- and y-directions. Additionally, the anamorphic mirror 54 may have aspheric terms along one or both of the directions, to correct for aberrations and improve the wavefront quality of the beam. The anamorphic mirror may be used at non-normal incidence, so that the incident and exiting beams do not interfere with or block each other. Alternatively, an anamorphic lens may be used instead of an anamorphic mirror, in which case the anamorphic lens may be used on-axis and may have aspheric terms along one or both of the directions to correct for aberrations.

The combination of the prism 52 and the mirror 54 may be considered to be part of an illumination arm 46 or an arm.

After reflecting off the mirror 54, the beam strikes the illumination region at a fairly high angle of incidence. The shape of the beam leaving the mirror 54 is elliptical, so that the illuminated illumination region is essentially round when viewed from a camera at or near normal incidence.

Figure 3:
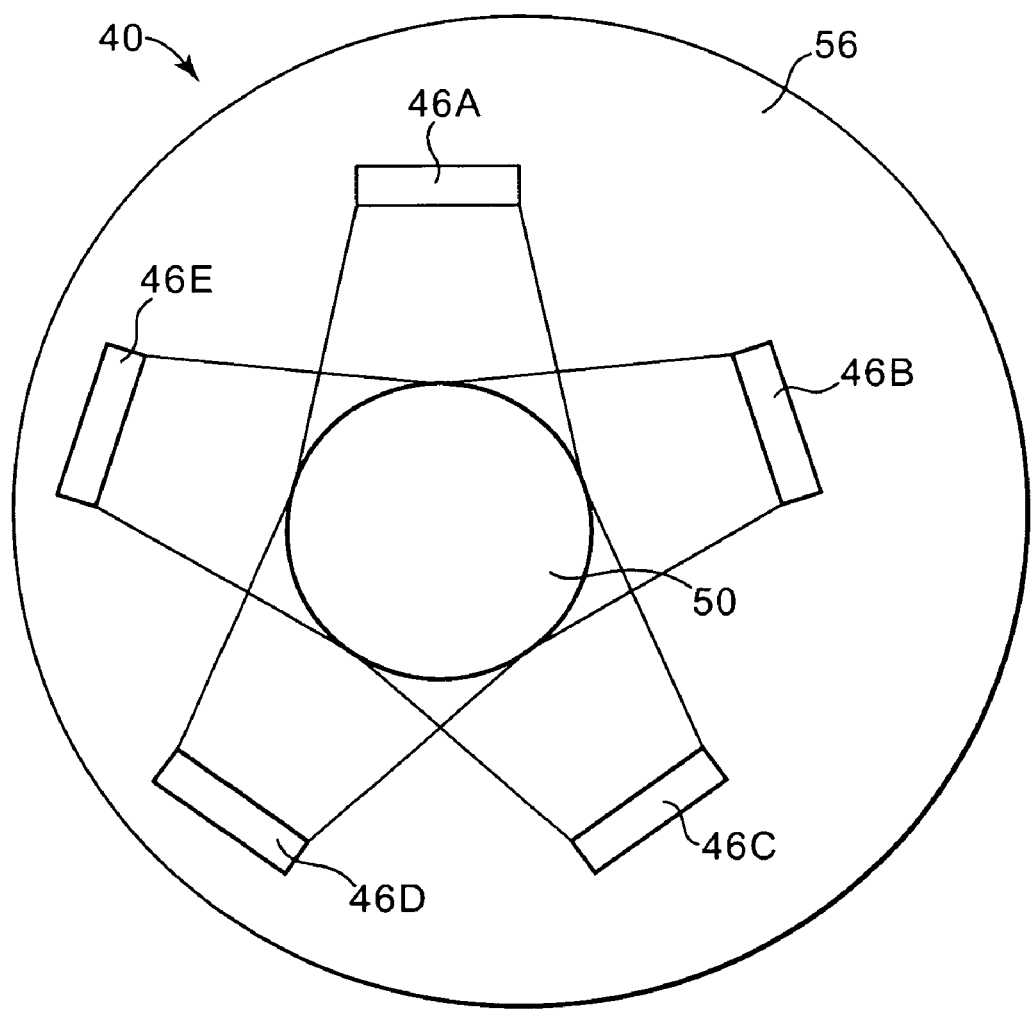
FIG. 3 is a top view drawing of the illumination arms, the illumination region and the wafer.

FIG. 3 shows the illumination region 50 of a wafer 56 from the point of view of the camera, at near-normal incidence. The illumination arms 46A-E are arranged around the circumference of the illumination region 50, which essentially corresponds to the illumination region. Note that because the illumination region 50 is smaller than the wafer 56; in order to inspect the entire wafer surface, the wafer 56 may be scanned with respect to the illumination region 50. The wafer may be placed on a computer-controlled translation stage that can automatically scan the entire wafer 56, while the inspection system acquires, stores and process the acquired images. Alternatively, the wafer may remain fixed and the illumination and acquisition optics translated.

Figure 4:
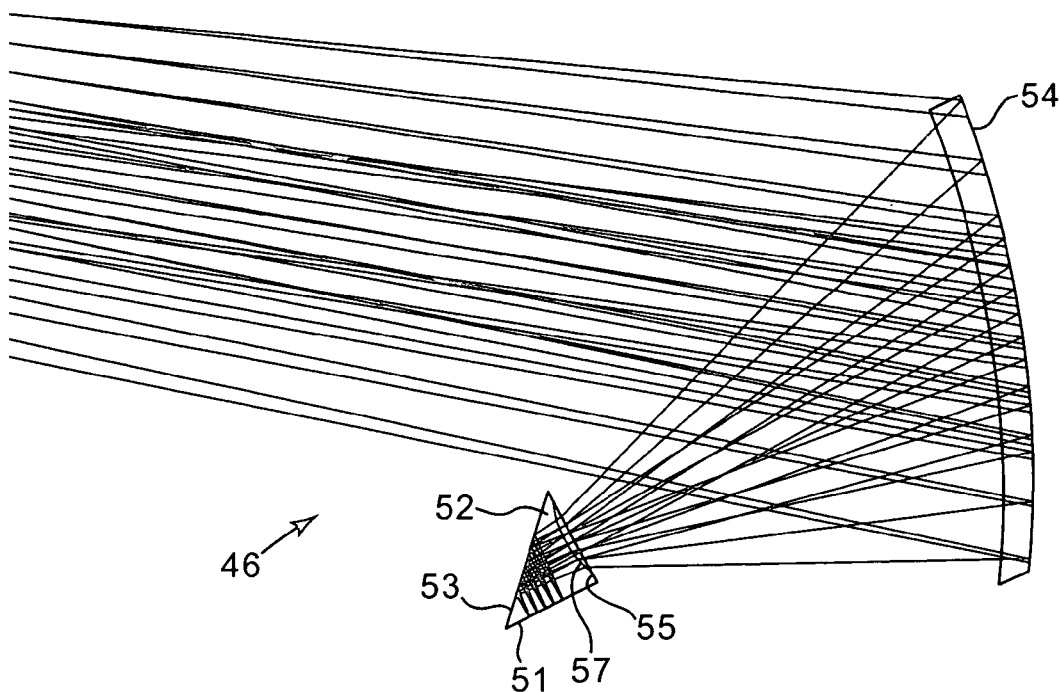
FIG. 4 is a plan drawing of a turning prism with a cylindrical element and an anamorphic reflector.
Figure 5:
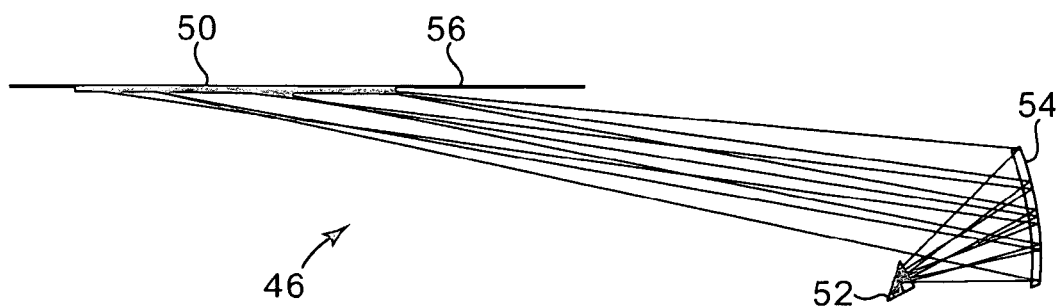
FIG. 5 is a plan drawing of a turning prism with a cylindrical element, an anamorphic reflector, the illumination region and the wafer.

FIG. 4 and FIG. 5 show close-up views of the optics of the illumination arm 46, with exemplary rays shown throughout. Light exits the fiber bundle (not shown) and enters the entrance face 51 of the prism 52. The exiting face of the fiber bundle may be treated as an extended source, emitting rays into a cone of uniform size and direction, regardless of location in the bundle. This may be seen visually in FIG. 4 by careful examination of the ray bundles in close proximity to entrance face 51. The light then reflects off the hypotenuse 53 of the prism, and propagates toward the exiting face 55 of the prism 52. The exiting face 55 has a cylindrical element 57 with negative power that diverges the beam in only one direction; in the other direction, the beam continues to propagate with the divergence determined by the fiber bundle numerical aperture. After leaving the prism 52, the beam reflects off an anamorphic reflector 54, which has different power in the x- and y-directions. The beam then strikes the illumination region 50 of the wafer 56 at a fairly high angle of incidence.

Figure 6:
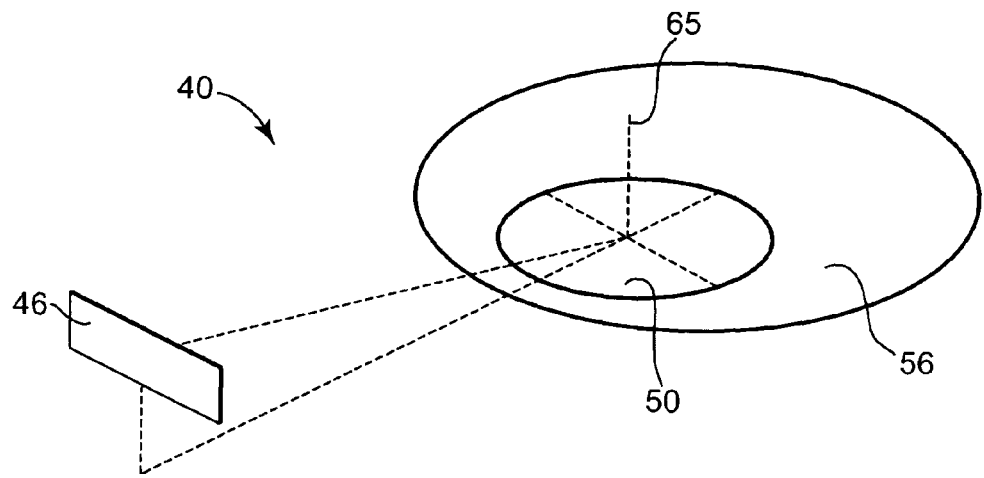
FIG. 6 is a perspective drawing of an illumination arm, the illumination region and the wafer.
Figure 7:
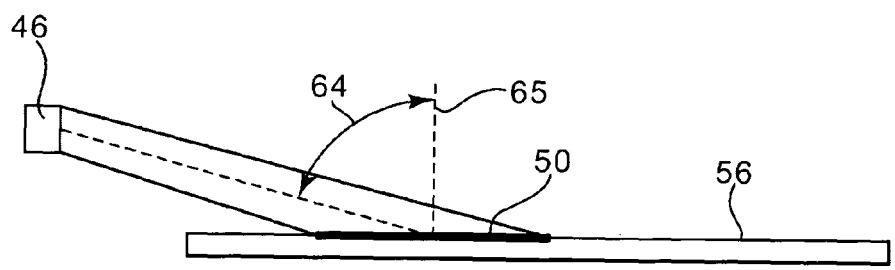
FIG. 7 is a side-view drawing of an illumination arm, the illumination region and the wafer.

FIG. 6 shows a perspective view of the illumination system 40, with only one schematically rendered illumination arm 46 shown. The illumination region 50 on the wafer 56 is generally circular, as seen from the surface normal 65. The same geometry of FIG. 6 is shown in a side view in FIG. 7. The angle of incidence 64 can be quite large.

Figure 8:
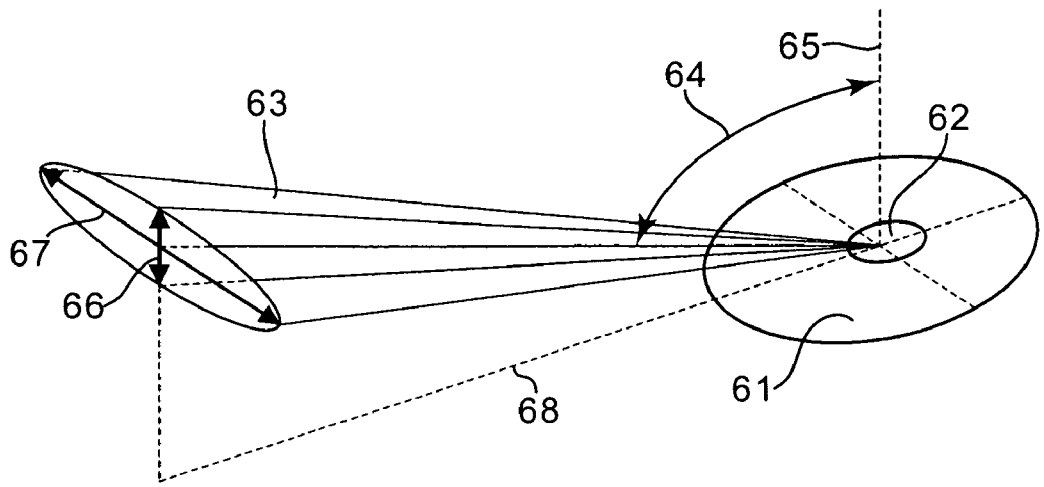
FIG. 8 is a perspective drawing of a cone of light received by a particular location in the illumination region of the wafer under test.

FIG. 8 shows a portion of the optical system along with some constructs that are useful for defining the relevant geometry of the illumination system. The wafer under test 61 has an illumination region 62, which is approximately circular when viewed from roughly normal incidence. Normal incidence means that the observer or camera is located apart from the wafer 61 and has a viewing angle roughly parallel to a surface normal 65. The illumination region 62 receives light from each of the illuminating arms, which may be located circumferentially around the illumination region 62. Any number of illuminating arms 46 may be used, including up to five or more.

A light cone 63 is shown converging to a particular location in the illumination region 62. This cone 63 does not represent the full extent of the illuminating beam, but represents all the light arriving at a particular location from one illuminating arm. The cone 63 arrives with a particular angle of incidence 64, which can be substantial. In a dark-field illuminator, the illumination is at a high enough incident angle so that a specular reflection, which occurs on a flat portion of the wafer 61, reflects at a suitably high angle of reflection and is not collected by the camera. In general, the higher the angle of incidence for the illumination, the better. For a system in which the collection optics have a numerical aperture of 0.8, the minimum angle of incidence for the dark field illumination is $\sin^{-1}(0.8)$, or about 53°. Preferably, the angle of incidence is even higher than that, and may be as high as 81°, or higher.

The incident cone 63 has a particular plane of incidence, defined by dotted line 68 and surface normal 65. Strictly speaking, each ray in the cone has its own plane of incidence, but for the purposes of this document, the plane of incidence for the entire cone 63 is defined as the plane of incidence for the central ray in the cone 63.

The cone 63 is generally asymmetric, and has an elliptical angular profile that may be defined by an incident angular range 66 and an azimuthal angular range 67, which is also referred to as a circumferential angle range. For all the rays in the cone 63, the true angle of incidence at the wafer 61 is in the range of incident angle 64±half the incident angular range 66. Note that the azimuthal angular components do not affect the angle of incidence at the wafer 61. In general, it is desirable to minimize the incident angular range 66, so that the illumination is more uniform. In discussions below, the meridional direction, which contains the incident angular range, is referred to as the "x"-direction, while the azimuthal angular range extends along the "y"-direction.

Note that each location in the illumination region 62 has its own cone of incident rays, and that the cone 63 is drawn in FIG. 8 for only one particular location. It is important to note that the cone 63 has essentially the same size for all locations within the field of view, meaning that the incident angle range 66 and azimuthal angle range 67 are essentially invariant across the field of view. In other words, the angular spectrum is uniform across the field. This is a highly desirable feature, and helps ensure that the sensitivity of the device is independent of the location within the field of view.

It is instructive to attach some numerical values to these angular ranges, which are obtained from the paraxial raytrace discussed below. These values are exemplary, and are presented to clarify the meaning of some of the quantities of FIG. 9.

In the x-direction, both the nominal angle of incidence 64 and the incident angle range 66 are truly invariant across the entire field of view, or, equivalently, the entire illumination region 50. For every point inside the illumination region, the nominal angle of incidence 64 is 81°. Likewise, for every point inside the illumination region, the full incident angle range is 5°. In other words, for every point inside the illumination region 50, the light arrives with an incident angle in the range of 81°±2.5°.

In the y-direction, the azimuthal angle range 67 is invariant across the field, but the nominal azimuthal angle does vary with location. At the center of the illumination region 50, the light arrives with an azimuthal angle in the range of 0°±0.4°. At one edge of the field, the light arrives at 7.5°±0.4°, and at the other edge, it arrives at −7.5°±0.4°. The azimuthal angle range 67 is therefore 0.8° for all points in the illumination region 50.

The angular spectrum may be considered a combination of the incident angle range 66 and the azimuthal angle range 67. From the above discussion, in which we showed that both of these quantities are invariant for all point in the illumination region 50, we may also say that the angular spectrum is invariant in the illumination region 50. In addition, the nominal incident angle 64 is invariant across the field.

The cone 63 drawn in FIG. 8 represents the output of one illumination arm, for one particular inspection point in the illumination region 62. The full output beam from an illumination arm is a collection of cones 63, with one for each location in the illumination region 62. The output beam is produced by an illumination arm described below, where the complete illumination system has multiple illumination arms, all lighting the same region 62 of the wafer 61, but from different azimuthal directions. Much of the following description applies to a single illumination arm, although it may apply to any or all the arms in the complete system.

Figure 9:
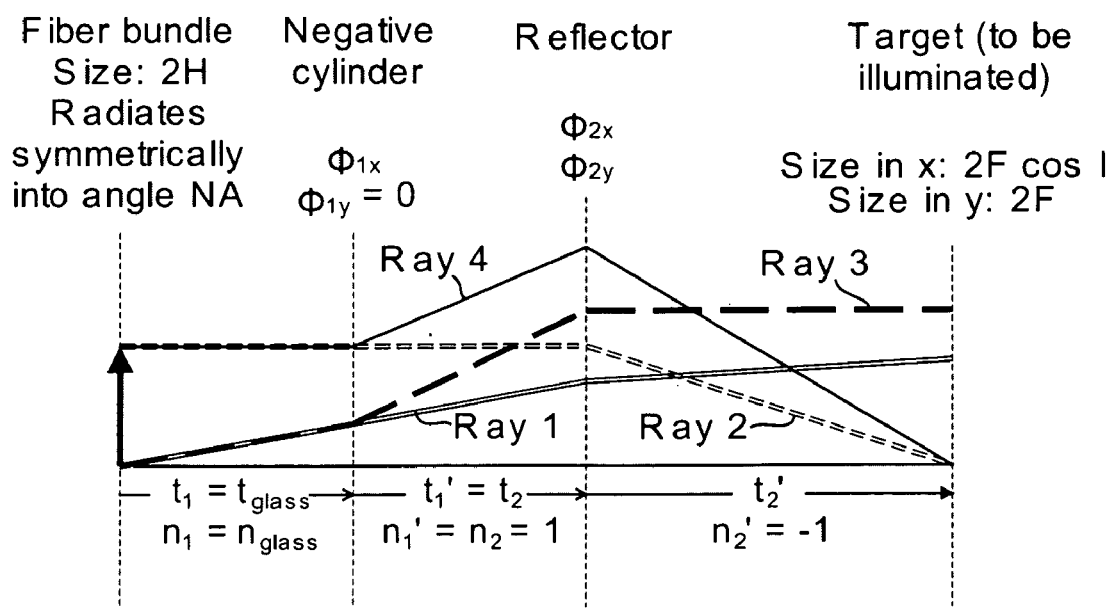
FIG. 9 is a schematic drawing of a paraxial representation of the optical system of an illumination arm.

The elements from the fiber bundle to the wafer, or target, are of special interest to us, in that the layout of these elements is non-trivial. In order to address the specifics of these elements, we use a paraxial raytrace. FIG. 9 shows a schematic of an optical system that is used for paraxial raytracing. From the raytrace, the required powers in x and y of the negative cylinder and the reflector are determined.

The multimode fiber bundle, shown at the leftmost edge of FIG. 9, radiates effectively uniformly into a rotationally symmetric cone with a characteristic numerical aperture NA. For the preferred fiber bundle, NA is roughly 0.1519. If the fiber bundle were to radiate into air, the radiant cone would have a half-angle equal to $\sin^{-1}$ NA. Because the fiber is coupled to the prism, so that the light leaving the fiber enters the prism, the radiant cone inside the prism has a half-angle equal to $\sin^{-1}$ (NA/$n_{glass}$), where $n_{glass}$ is the refractive index of the prism. A high-index glass may be used for the prism, such as LaSFN9, which has a refractive index $n_{glass}$ of 1.8558 at the design wavelength of 550 nm. Alternatively, other suitable glasses may be used, such as BK7 or other well-known glasses. Note that the required size of the fiber bundle is as yet undetermined.

The beam exiting the fiber bundle enters the glass prism, which first bends the beam by 90°, then diverges the beam in the x-dimension by passing it through a cylindrical surface on the exiting face of the prism. The prism has a refractive index $n_{glass}$, such as, for example, 1.8558. The beam propagates an on-axis distance denoted by $t_{glass}$, which includes the paths both before and after reflection from the hypotenuse of the prism. In order to satisfy the space requirement of the illumination system, a small prism is used, such as, for example, having a nominal square dimension of about 0.5 mm. Because of the cylindrical element on the exiting face of the prism, which extends into the exiting face, the actual on-axis distance traveled by the beam inside the prism is less than 0.5 mm. The preferred thickness $t_{glass}$ is about 0.474 mm, although other suitable values may be used for different-dimensioned prisms.

The cylindrical surface on the exiting face of the prism has a surface power $\Phi_{1x}$; the corresponding power component along y, $\Phi_{1y}$, is zero. The beam exits into air, so the exiting refractive index $n_1'$ is 1. The curvature that yields a surface power of $\Phi_{1x}$ is found from $c_{1x}=\Phi_{1x}/(n_1'-n_1)$, or $c_{1x}=\Phi_{1x}/(1-n_{glass})$. The radius of curvature, $R_{1x}$, is given by $R_{1x}=1/c_{1x}$. There is no optical power along the y-dimension.

The beam exiting the negative cylindrical surface on the prism travels through a distance $t_1'$ in air before entering the anamorphic reflector. Following the usual sign conventions used in ray tracing, the distance $t_1'$ may be denoted by $t_2$; both are numerically equal and are interchangeable. Both are also as yet undetermined. Because the beam travels in air, the refractive index $n_1'=n_2=1$.

The anamorphic reflector has a reflective surface with different powers along its x- and y-directions, denoted by $\Phi_{2x}$ and $\Phi_{2y}$. The reflector may be a mirror having a highly reflective dielectric thin film stack, although other suitable types of reflectors may be used as well. For this type of reflector, in which the incident and reflective surfaces are both air, the incident refractive index $n_2$ is 1, while the exiting refractive index $n_2'$ is −1. The mirror curvature that produces a given power is given by $c_{2x}=\Phi_{2x}/(n_2'-n_2)$, or $-\Phi_{2x}/2$. Similarly, $c_{2y}=-\Phi_{2y}/2$. The radii of curvature are given by $R_{2x}=1/c_{2x}$, and $R_{2y}=1/c_{2y}$.

After exiting the reflector, the beam propagates a distance $t_2'$ to the target. Note that with the typical conventions of raytracing, both the values of distance $t_2'$ and refractive index $n_2'$ are negative after reflection off the mirror; this is merely a numerical convenience, and simply implies that the reflected beam travels in generally the opposite direction as the incident beam. The distance $t_2'$ is as yet undetermined.

The target is the portion of the wafer that is to be inspected. It is preferred that the incident beam illuminates a generally circular region of the wafer. Because the incident beam strikes the target at a fairly high angle of incidence I, the beam footprint exiting the system should be asymmetric, so that a normally-incident camera may see a generally symmetric illumination region. Consider the following geometry, where the plane of incidence includes the x-dimension, so that y-axis is parallel to the target surface. Along the y-dimension, the illumination region seen by the camera is the same size as the incident beam along the y-dimension, say 2F. Along the x-dimension, an incident beam of size (2F cos I) illuminates an region of dimension 2F as seen by a normally-incident camera. The incident beam is therefore smaller along the x-dimension by a factor of cos I, so that a normally-incident camera sees a circle of illumination with diameter 2F. For a large angle of incidence, the compression factor cos I may be quite significant. For example, for the preferred angle of incidence of about 81°, cos(81°) equals 0.1564, resulting in a beam with an aspect ratio of about 6. Even with such a high aspect ratio, the correspondingly high angle of incidence produces a nearly round beam, as seen by a camera at nearly normal incidence. A preferred value for F is 10 mm, although other suitable values may be used.

From the raytrace described below, values may be obtained for the cylindrical powers of the negative cylinder and the reflector, as well as the distances between the surfaces.

Given the power $\Phi$ of each surface, the refractive index n between the surfaces, and thickness t between the surfaces, one may use the well-known paraxial refraction and transfer equations to trace a ray through the optical system of FIG. 9.

The paraxial refraction equation predicts the exiting ray angle (relative to the optical axis) u', after refraction at a surface with power Φ:

$$n'u' = nu - y\Phi,$$

where u is the incident ray angle, y is the incident and exiting ray height at the surface, and n and n' are the incident and exiting refractive indices, respectively. The refractive indices are dimensionless, the ray angles are in radians, the ray heights are in mm, and the surface powers are in mm$^{-1}$.

The paraxial transfer equation predicts the ray height y' at a surface, after propagation by a distance t between a previous surface and the current surface:

$$y' = y + tu,$$

where y is the ray height at the previous surface and u is the ray angle (relative to the optical axis) between the previous surface and the current surface. The ray angle is in radians and the ray heights and distances are both in mm.

The above paraxial refraction and transfer equations are alternately used to trace rays through the multi-surface optical system of FIG. 8. Separate raytraces are performed for the x- and y-dimensions, with the thicknesses between the surfaces remaining the same, but the powers of each surface being different.

Some initial assumptions are made for the optical system. First, it is desirable to image the pupil of the fiber bundle onto the target. For a fiber bundle, the pupil of the bundle is located at infinity, so we therefore locate the target at the rear focal plane of the system in both x- and y-directions. Second, it is desirable to illuminate a circular portion of the target. Because the illumination is at a fairly high angle of incidence, the incident beam should have an asymmetric footprint. Therefore, the optical system should have different magnifications in the x- and y-dimensions, or, equivalently, different focal lengths along the x- and y-dimensions. We therefore choose to place the fiber bundle at the front focal plane of the system in the x-direction, so that any spatial variations in intensity at the fiber bundle are minimized at the target. We do not explicitly constrain the front focal plane of the system in the y-direction.

The goal of the ray trace, sketched schematically in FIG. 9, is to obtain values for cylindrical powers $\Phi_{1x}$, $\Phi_{2x}$ and $\Phi_{2y}$, and distances $t_2$ and $t_2'$. The fixed values in the ray trace are the refractive index of the prism $n_{glass}$ (equal to 1.8558, for example), thickness traveled inside the prism $t_{glass}$ (equal to 0.474 mm, for example), numerical aperture of the beam exiting the fiber bundle NA (equal to 0.1519, for example), and illuminated diameter at the target 2F (equal to 20 mm, for example). Four rays are traced and are each shown schematically, but not to scale, in FIG. 9.

First, we trace Ray 1 along the y-dimension. Omitting the intermediate algebra, we find that the total power of the system in the y-dimension $\Phi_y$ equals the power of the reflector in the y-dimension $\Phi_{2y}$, and both are given by $\Phi_y = \Phi_{2y} = \text{NA}/F$. For the preferred values of NA (0.1519) and F (10 mm), $\Phi_{2y} = -0.01519$ mm$^{-1}$, leading to a reflector radius $R_{2y}$ of $-131.7$ mm.

Next, we trace Ray 2 in the y-dimension. Again omitting the intermediate algebra, we find that the on-axis distance between the reflector and the target $t_2'$ is given by $t_2' = -F/\text{NA}$. Using the preferred values above, $t_2'$ is $-65.8$ mm. The value is negative, meaning that the incident and exiting beams are on the same side of the reflector; this is the usual case for a mirror.

Next, we trace Ray 3 in the x-dimension. We obtain two pieces of information from Ray 3. First, the total optical power of the system in the x-direction is given by $\Phi_x = \text{NA}/(F \cos I)$. For the preferred values, the total optical power in x is about $+0.0971$ mm$^{-1}$. Second, the relationship between thickness $t_2$ and power $\Phi_{2x}$ is given by $(t_2)(\Phi_{2x}) = 1 - [(t_{glass}/n_{glass})(\text{NA})/(F \cos I)]$.

Finally, we trace Ray 4 in the x-dimension, and obtain a relationship between thickness $t_2$ and power $\Phi_{1x}$, given by $(t_2)(\Phi_{1x}) = 1 - (1/\cos I)$.

We combine the preceding two equations with the well-known relationship $\Phi_x = \Phi_{1x} + \Phi_{2x} - (t_2/n_2)(\Phi_{1x})(\Phi_{2x})$ to obtain expressions for the remaining powers and thickness.

The power along the x-direction for the negative cylinder is given by:

$$\Phi_{1x} = [1 - (1/\cos I)] / [(F \cos I/\text{NA}) - \{(t_{glass}/n_{glass})/\cos I\}].$$

For the preferred values given above, $\Phi_{1x}$ is $-0.622$ mm$^{-1}$, giving a radius $R_{1x}$ of $+1.375$ mm.

The power along the x-direction for the reflector is given by:

$$\Phi_{2x} = [1 - (t_{glass}/n_{glass})(\text{NA})/(F \cos I)] / [(F \cos I/\text{NA}) - \{(t_{glass}/n_{glass})/\cos I\}]$$

For the preferred values given above, $\Phi_{2x}$ is $+0.1125$ mm$^{-1}$, giving a radius $R_{2x}$ of $-17.77$ mm.

The on-axis thickness $t_2$ (or, equivalently, $t_1'$) between the negative cylinder and the reflector target is given by:

$$t_2 = (F \cos I/\text{NA}) - [(t_{glass}/n_{glass})/\cos I]$$

For the preferred values given above, $t_2$ is $+8.666$ mm.

There is a remaining quantity that may be obtained from the trace of Ray 4 in the x-direction. Because the fiber bundle is located at the front focal plane of the system (in x), all the rays that originate from a particular point on the bundle arrive at the target at the same angle (in x). As a result, it becomes apparent that the size of the fiber bundle determines the range of incident angles (in x) that arrive at the target. If the bundle were infinitesimally small, all the rays would arrive at precisely the same incident angle, and the range of incident angles would be essentially zero. Obviously, for radiometric reasons the bundle cannot be infinitesimally small; no light would get through the system. A reasonable value of the half-range of incident angles (in x) is roughly 2.5°, based on a compromise between radiometric power at the target (where a big bundle is suitable) and uniformity of incident angle at the target (where a small bundle is suitable). For a half-range HR of incident angles, the required half-height of the bundle H is given by H=(tan HR)(F cos I)/NA. For the typical values given above, and a half-range HR of 2.5°, the required half-height of the fiber bundle is about 0.45 mm. In other words, if the fiber bundle has a radius of 0.45 mm, then all the illumination arrives at the target with an incident angle of 81°±2.5°. For improved performance, the gap between the illumination angles and the collection angles may be made substantial, so that a specular reflection off the target remains well outside of the collection optics.

Note that once the radii of curvature are determined for the various surfaces, aspheric and/or conic terms may be optionally added to one or more of them to reduce aberrations in the beam. These aspheric terms are most easily handled by a commercially available raytracing program, such as Oslo, ZEMAX, Code V, and others.

Now that the values of powers, radii of curvature, and thickness have been determined in analytical form, based on the paraxial raytrace of the system shown in FIG. 9, it is instructive to show the numerical values of the corresponding ray traces. These values are given in the ray trace spreadsheet shown in FIG. 10. The input values not determined by the spreadsheet are shown in the thick-bordered cells.

A variety of rays are traced, including rays through the center and both edges of the target, and through the center and one edge of the fiber bundle. Because the system is symmetric, a ray through the other edge of the fiber bundle is unnecessary. Note that rays 1 through 4 from FIG. 9 are denoted in FIG. 10.

There are several noteworthy features of the spreadsheet of FIG. 10. All the rays originate at the fiber bundle with a height between −0.449 mm and +0.449 mm, and with a numerical aperture between −0.1519 and +0.1519. All the rays arrive at the target with a height between −10 mm and +10 mm in y, and between −1.564 mm and +1.564 mm in x. As discussed earlier, the beam is effectively expanded in x to appear the same size as in the y-dimension, with respect to a normally-incident camera.

In the x-dimension, all the rays arrive with an incident ray slope between −0.0437 radians and +0.0437 radians, or, equivalently, an incident ray angle between −2.5° and +2.5°. Because the x-dimension lies in the plane of incidence, the range of ±2.5° becomes the range of incident angles at the target.

In contrast, note that in the y-dimension, the incident rays have a much larger angular range, with slopes between −0.138 radians and +0.138 radians, or, equivalently, incident ray angles between −7.9° and +7.9°. Because the y-dimension is parallel to the target surface, this rather large angular range has no effect on the range of incident angles, unlike the x-dimension. It is easiest to visualize this y-range from the point of view of a normally-incident camera, looking at the target. If one imagines a clock face superimposed on the target, with the illumination arm located near 12-o'clock, then portions of the 20 mm-diameter circle at the center that receives illumination receive it from rays originating between roughly 11:45 and 12:15. In the actual visual inspection station, five illumination arms are used, each spaced apart by about 72° around the full 360° clock-face envisioned earlier. It is understood that more or fewer than five illumination arms may be used as well.

It is instructive to summarize the paraxial layout thus far. A beam emerges from a multi-mode fiber bundle, passes through a 90° turning prism that has a negative-power cylindrical surface on its exiting face, reflects off an anamorphic mirror, and illuminates a target at a non-zero incident angle. The illumination region is generally round when viewed by an essentially normally incident camera. The target is at the rear focal plane of the system in both x- and y-dimensions. The fiber bundle is at the front focal plane of the system in the x-dimension. The size of the illumination region at the target is directly proportional to the numerical aperture of the fiber bundle. The range of exiting angles from the illumination arm is directly proportional to the size, or spatial extent, of the fiber bundle.

Note that although the paraxial layout is performed as if all the elements are centered about the optical axis, in reality, they may be bent or folded to include non-normally-incident surfaces. For instance, the anamorphic mirror is treated validly as an on-axis element in the paraxial raytrace, but once the powers and distances are determined, the actual part may have a finite angle of incidence on-axis. These angles are best determined by clear aperture requirements, where neither an incident nor a reflected beam should be inadvertently blocked by any components. Because the incident beam is tilted with respect to the target, the center of the illumination region should be located at the prescribed z-distance, namely at the rear focal planes in both x and y.

The resulting system has many advantages over known illumination systems. For instance, the system is compact, has a large format (20 mm diameter illumination region), has uniform illumination over the illumination region, has a uniform angular spectrum over the illumination region, has a small incident angle range, has a broad circumferential azimuth (or, equivalently, a large azimuthal angle range), and is relatively bright. As a result of these advantages, the wafer inspection system is essentially insensitive to particle location and orientation within the field of view.

In all of the discussion thus far, it has been implicitly assumed that the optical power on the exiting face of the prism is essentially cylindrical, with a negative power in the meridional direction and no power in the azimuthal direction. As an alternative embodiment, power may be provided in both dimensions on the exiting face of the prism, not just in the meridional direction. In other words, the exiting face may have an element with anamorphic optical power, in which the powers in the meridional and azimuthal directions are unequal; this may be referred to as a first anamorphic element. Likewise, the anamorphic mirror or lens may be referred to as a second anamorphic element.

Figure 11:
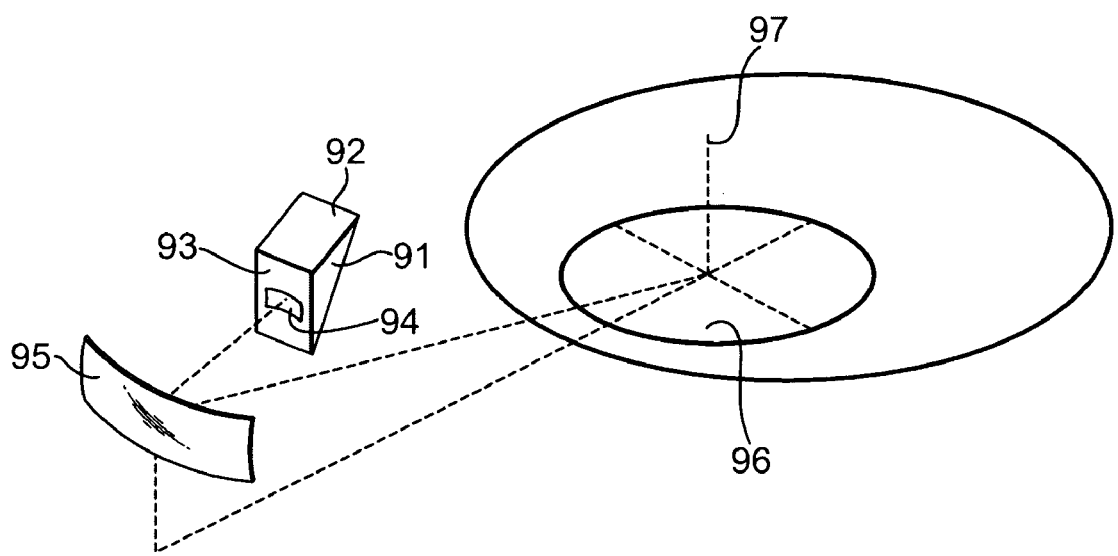
FIG. 11 is a simplified perspective view of portions of another illumination system in accordance with the present disclosure.

The optical path for this embodiment is similar to that of the essentially cylindrical embodiment and is shown in FIG. 11. Light exits the end of a multimode fiber bundle (not shown), enters a turning prism 91 through its incident face 92, reflects off its hypotenuse (although other suitable geometries may be used), and exits the turning prism 91 through its exiting face 93. The exiting face 93 has a first anamorphic element 94 with optical power in both the meridional and azimuthal dimensions. The first anamorphic element 94 may be an anamorphic depression in the surface of the exiting face 93, or may be an anamorphic lens attached to the exiting face. The beam exiting the prism 91 propagates to a second anamorphic element 95, which may be a mirror or a lens. The beam exiting the second anamorphic element 95 then strikes the illumination region 96 at a high angle of incidence, with respect to the surface normal 97.

For such an embodiment, it is still desirable to image the pupil of the fiber bundle onto the illumination region, which is ensured by placing both the meridional rear focal plane and the azimuthal rear focal plane at the illumination region. In addition, because it is also desirable to have a uniform nominal incident angle across the illumination region, we place the fiber bundle at the meridional front focal plane. For this embodiment, the location of the azimuthal front focal plane is indeterminate; it may or may not coincide with the meridional front focal plane.

As a further embodiment, a rotationally symmetric element may be provided on or attached to the exiting face of the prism, rather than an anamorphic element or a purely cylindrical element.

The description and its applications as set forth herein is illustrative and is not intended to limit the scope. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit, as set forth in the following claims.

Although the present disclosure has been described with reference to preferred embodiments, workers skilled in the art will recognize that changes can be made in form and detail without departing from the spirit and scope of the present disclosure.

What is claimed is:

1. An illuminator for dark field inspection of a surface of a target, comprising:
a plurality of illumination arms disposed about an illumination region, each arm having an input end and an output end, the output end outputting substantially uniform diverging light;
a plurality of turning elements each having a first face optically coupled to the respective output ends of the respective illumination arms, and a second face having optical power in a meridional direction;
a plurality of anamorphic elements each having a first optical power in an azimuthal direction and a second optical power in the meridional direction, the first and second optical powers being unequal, and the anamorphic element being optically coupled to the second face of the turning element; and
wherein light from the illuminator that is incident on the illumination region is substantially uniform in its angular spectrum.

2. The illuminator of claim 1, wherein each of the turning elements is physically coupled to the output end of the illumination arm.

3. The illuminator of claim 1, wherein the light from the illuminator that is incident on the illumination region is substantially uniform in its intensity.

4. The illuminator of claim 1, wherein the illumination region is about 20 mm.

5. The illuminator of claim 1, wherein the light incident on the illumination region is, over substantially the entire illumination region, incident within a range of about −2.5° and +2.5° as measured within the incident plane.

6. The illuminator of claim 1, wherein the light incident on the illumination region is, over substantially the entire illumination region, incident within a range of about −7.9° and +7.9° as measured parallel to the plane of the illumination region.

7. The illuminator of claim 1, further comprising an input head optically coupled to the input ends of the plurality of illumination arms.

8. The illuminator of claim 7, wherein the input head comprises a condensing lens for collecting light from an illumination source and a mixing bar having an input end arranged to receiving light from the condensing lens and an output end optically coupled to the input ends of the plurality of the illumination arms, the mixing bar having a longitudinal extent sufficient to ensure substantially uniform spatial mixing of transmitted light.

9. The illuminator of claim 1, wherein the angle of incidence is greater than approximately 55 degrees relative to a normal of the illumination region to achieve specular reflection from a target surface under defect-free conditions.

10. The illuminator of claim 9, wherein the angle of incidence is greater than approximately 81 degrees.

11. An illuminator for dark field inspection of a surface of a target, comprising:
a plurality of illumination arms disposed about an illumination region, each illumination arm comprising a multimode fiber bundle having an input end and an output end, the output end outputting substantially uniform diverging light;
a plurality of turning elements each having a first face physically and optically coupled to the respective output ends of the respective illumination arms, and a second face having optical power in a meridional direction;
a plurality of anamorphic elements each having a first optical power in an azimuthal direction and a second optical power in the meridional direction, the first and second optical powers being unequal, and the anamorphic element being optically coupled to the second face of the turning element; and
wherein light from the illuminator that is incident on the illumination region is substantially uniform in its intensity and angular spectra.

12. The illuminator of claim 11, wherein the light incident on the illumination region is, over substantially the entire illumination region, incident within a range of about −2.5° and +2.5° as measured within the incident plane.

13. The illuminator of claim 11, wherein the light incident on the illumination region is, over substantially the entire illumination region, incident within a range of about −7.9° and +7.9° as measured parallel to the plane of the illumination region.

* * * * *

UNITED STATES PATENT AND TRADEMARK OFFICE
CERTIFICATE OF CORRECTION

PATENT NO.        : 7,724,358 B2                                            Page 1 of 1
APPLICATION NO. : 12/276065
DATED             : May 25, 2010
INVENTOR(S)       : David Vaughnn It is certified that error appears in the above-identified patent and that said Letters Patent is hereby corrected as shown below:

Column 10, line 25, delete "$1/c_{2x}$." and insert -- $1/c_{2x}$ --, therefor.

Signed and Sealed this

Thirteenth Day of July, 2010

David J. Kappos
*Director of the United States Patent and Trademark Office*